(12) United States Patent
Dineen et al.

(10) Patent No.: US 8,757,163 B2
(45) Date of Patent: Jun. 24, 2014

(54) AIRWAY IMPLANTS AND METHODS AND DEVICES FOR INSERTION AND RETRIEVAL

(75) Inventors: Michael Dineen, Portola Valley, CA (US); Mark Hirotsuka, San Jose, CA (US); Jasper Jackson, Newark, CA (US); Damien Shulock, San Francisco, CA (US); Andrew Frazier, Sunnyvale, CA (US); Chad Roue, San Jose, CA (US); Erik Van Der Burg, Los Gatos, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/350,867

(22) Filed: Jan. 16, 2012

(65) Prior Publication Data

US 2012/0111341 A1    May 10, 2012

Related U.S. Application Data

(60) Division of application No. 11/835,931, filed on Aug. 8, 2007, now Pat. No. 8,096,303, and a continuation-in-part of application No. 11/349,044, filed on Feb. 7, 2006, now abandoned.

(60) Provisional application No. 60/836,579, filed on Aug. 8, 2006, provisional application No. 60/650,867, filed on Feb. 8, 2005, provisional application No. 60/726,028, filed on Oct. 12, 2005.

(51) Int. Cl.
*A61F 5/56* (2006.01)
*A61B 17/56* (2006.01)
*A61F 2/06* (2013.01)

(52) U.S. Cl.
USPC .............................. 128/848; 606/60; 623/1.36

(58) Field of Classification Search
USPC ............. 606/151, 232, 41, 60, 300–301, 310, 606/313, 77, 78, 153–156, 193, 198; 602/902; 623/1.36; 128/831, 348, 887
See application file for complete search history.

(56) References Cited

U.S. PATENT DOCUMENTS

| 346,771 A | 8/1886 | Phillips |
| 1,156,440 A | 10/1915 | Smith |

(Continued)

FOREIGN PATENT DOCUMENTS

| CN | 101040807 | 9/2007 |
| DE | 1 242 322 | 6/1967 |

(Continued)

OTHER PUBLICATIONS

Letter to Aspire Medical, Inc. from a third party, date Jul. 13, 2007 (redacted in part).

(Continued)

*Primary Examiner* — Patricia Bianco
*Assistant Examiner* — Tarla Patel

(57) ABSTRACT

Embodiments of the present invention relate to methods and devices for the treatment of airway obstruction, such as obstructive sleep apnea, and devices and methods that facilitate insertion and retrieval of the same. In one embodiment, disclosed is a tissue tensioner that includes an elongate flexible tether having a first end and a second end, a bone anchor configured to be connected to a patient's mandible, a tissue ingrowth implant configured to be implanted in a patient's tongue and connected to the second end of the tether, and an adjustment mechanism configured to be held by the bone anchor adjacent the patient's mandible and configured to receive the first end of the tether and configured to adjust tension in the flexible tether between the patient's mandible and tongue. Various anchors, tethers, securement mechanisms, and adjustment mechanisms that can be used with glossal and palatal remodeling systems are also disclosed.

6 Claims, 8 Drawing Sheets

(56) References Cited

U.S. PATENT DOCUMENTS

| | | | |
|---|---|---|---|
| 1,374,963 | A | 4/1921 | Stevenson |
| 2,154,428 | A | 4/1939 | Andres |
| 2,181,746 | A | 11/1939 | Siebrandt |
| 2,583,896 | A | 1/1952 | Siebrandt |
| 2,824,717 | A | 2/1958 | Yeager |
| 2,966,907 | A | 1/1961 | Fasolino |
| 3,477,429 | A | 11/1969 | Sampson |
| 3,593,709 | A | 7/1971 | Halloran |
| 4,263,904 | A | 4/1981 | Judet |
| 4,279,248 | A | 7/1981 | Gabbay |
| 4,348,179 | A | 9/1982 | Nardella |
| 4,366,815 | A | 1/1983 | Broomes |
| 4,676,240 | A | 6/1987 | Gardy |
| 4,700,697 | A | 10/1987 | Mundell |
| 4,830,008 | A | 5/1989 | Meer |
| 4,840,172 | A | 6/1989 | Augustine |
| 4,858,601 | A | 8/1989 | Glisson |
| 4,885,824 | A | 12/1989 | Schwab |
| 4,898,156 | A | 2/1990 | Gatturna |
| 4,978,323 | A | 12/1990 | Freedman |
| 5,046,513 | A | 9/1991 | Gatturna |
| 5,123,425 | A | 6/1992 | Shannon, Jr. |
| 5,127,413 | A | 7/1992 | Ebert |
| 5,141,581 | A * | 8/1992 | Markham ............ 156/242 |
| 5,176,617 | A | 1/1993 | Fischell |
| 5,176,618 | A | 1/1993 | Freedman |
| 5,178,156 | A | 1/1993 | Takishima |
| 5,190,546 | A | 3/1993 | Jervis |
| 5,192,303 | A | 3/1993 | Gatturna |
| 5,254,097 | A | 10/1993 | Schock et al. |
| 5,282,845 | A | 2/1994 | Bush |
| 5,320,602 | A | 6/1994 | Karpiel et al. |
| 5,358,511 | A | 10/1994 | Gatturna |
| 5,411,522 | A | 5/1995 | Trott |
| 5,443,482 | A | 8/1995 | Stone |
| 5,460,524 | A | 10/1995 | Anderson |
| 5,462,561 | A | 10/1995 | Voda |
| 5,464,424 | A | 11/1995 | O'Donnell, Jr. |
| 5,478,353 | A | 12/1995 | Yoon |
| 5,501,696 | A | 3/1996 | Trott |
| 5,505,735 | A | 4/1996 | Li |
| 5,512,037 | A | 4/1996 | Russell et al. |
| 5,522,844 | A | 6/1996 | Johnson |
| 5,554,171 | A | 9/1996 | Gatturna |
| 5,571,104 | A | 11/1996 | Li |
| 5,573,540 | A | 11/1996 | Yoon |
| 5,578,032 | A | 11/1996 | Lalonde |
| 5,620,012 | A | 4/1997 | Benderev et al. |
| 5,626,597 | A | 5/1997 | Urban et al. |
| 5,647,874 | A | 7/1997 | Hayhurst |
| 5,662,654 | A | 9/1997 | Thompson |
| 5,665,089 | A | 9/1997 | Dall |
| 5,690,640 | A | 11/1997 | Gotfried |
| 5,718,705 | A | 2/1998 | Sammarco |
| 5,722,976 | A | 3/1998 | Brown |
| 5,725,557 | A | 3/1998 | Gatturna |
| 5,735,875 | A | 4/1998 | Bonutti |
| 5,797,919 | A | 8/1998 | Brinson |
| 5,810,824 | A | 9/1998 | Chan |
| 5,840,078 | A | 11/1998 | Yerys |
| 5,868,762 | A | 2/1999 | Cragg |
| 5,893,856 | A | 4/1999 | Jacob |
| 5,897,491 | A | 4/1999 | Kastenbauer et al. |
| 5,928,231 | A | 7/1999 | Klein |
| 5,954,057 | A | 9/1999 | Li |
| 5,979,456 | A | 11/1999 | Magovern |
| 5,988,171 | A | 11/1999 | Sohn |
| 6,042,534 | A | 3/2000 | Gellman et al. |
| 6,079,413 | A | 6/2000 | Braran |
| 6,132,438 | A | 10/2000 | Fleischman |
| 6,161,541 | A | 12/2000 | Woodson |
| 6,162,362 | A | 12/2000 | Ma |
| 6,188,932 | B1 | 2/2001 | Lindegren |
| 6,200,330 | B1 | 3/2001 | Benderev |
| 6,203,565 | B1 | 3/2001 | Bonutti |
| 6,240,316 | B1 | 5/2001 | Richmond |
| 6,306,141 | B1 | 10/2001 | Jervis |
| 6,312,431 | B1 | 11/2001 | Asfora |
| 6,315,780 | B1 | 11/2001 | Lalonde |
| 6,322,492 | B1 | 11/2001 | Kovac |
| 6,328,686 | B1 | 12/2001 | Kovac |
| 6,328,753 | B1 | 12/2001 | Zammit |
| 6,408,851 | B1 | 6/2002 | Karell |
| 6,408,852 | B2 | 6/2002 | Tielemans |
| 6,423,072 | B1 | 7/2002 | Zappala |
| 6,425,900 | B1 | 7/2002 | Knodel |
| 6,431,174 | B1 | 8/2002 | Knudson |
| 6,439,238 | B1 | 8/2002 | Brenzel |
| 6,447,524 | B1 | 9/2002 | Knodel |
| 6,458,100 | B2 | 10/2002 | Roue |
| 6,482,178 | B1 | 11/2002 | Andrews |
| 6,503,267 | B2 | 1/2003 | Bonutti |
| 6,536,439 | B1 | 3/2003 | Palmisano |
| 6,540,695 | B1 | 4/2003 | Burbank |
| 6,554,833 | B2 | 4/2003 | Levy |
| 6,599,311 | B1 | 7/2003 | Biggs |
| 6,626,910 | B1 | 9/2003 | Hugues |
| 6,626,916 | B1 | 9/2003 | Yeung et al. |
| 6,634,362 | B2 | 10/2003 | Conrad |
| 6,656,182 | B1 | 12/2003 | Hayhurst |
| 6,668,834 | B1 | 12/2003 | Zikria |
| 6,685,707 | B2 | 2/2004 | Roman |
| 6,746,472 | B2 | 6/2004 | Frazier |
| 6,770,022 | B2 | 8/2004 | Mechlenburg |
| 6,913,607 | B2 | 7/2005 | Ainsworth |
| 6,955,172 | B2 | 10/2005 | Nelson |
| 6,971,396 | B2 | 12/2005 | Knudson |
| 6,997,189 | B2 | 2/2006 | Biggs |
| 7,008,428 | B2 | 3/2006 | Cachia |
| 7,017,582 | B2 | 3/2006 | Metzger |
| 7,022,131 | B1 | 4/2006 | Derowe |
| 7,025,756 | B2 | 4/2006 | Frazier |
| 7,028,691 | B2 | 4/2006 | Knudson |
| 7,036,515 | B2 | 5/2006 | Conrad |
| 7,047,979 | B2 | 5/2006 | Conrad |
| 7,048,682 | B2 | 5/2006 | Neisz |
| 7,052,498 | B2 | 5/2006 | Levy |
| 7,055,525 | B2 | 6/2006 | L'Estrange |
| 7,060,021 | B1 | 6/2006 | Wilk |
| 7,062,317 | B2 | 6/2006 | Avrahami |
| 7,063,089 | B2 | 6/2006 | Knudson |
| 7,073,505 | B2 | 7/2006 | Nelson |
| 7,077,143 | B2 | 7/2006 | Knudson |
| 7,077,144 | B2 | 7/2006 | Knudson |
| 7,090,672 | B2 | 8/2006 | Underwood |
| 7,090,690 | B2 | 8/2006 | Foerster |
| 7,100,613 | B2 | 9/2006 | Conrad |
| 7,107,992 | B2 | 9/2006 | Brooks |
| 7,115,110 | B2 | 10/2006 | Frazier |
| 7,122,043 | B2 | 10/2006 | Greenhalgh |
| 7,128,753 | B1 | 10/2006 | Bonutti |
| 7,131,973 | B2 | 11/2006 | Hoffman |
| 7,144,363 | B2 | 12/2006 | Pai |
| 7,146,981 | B2 | 12/2006 | Knudson |
| 7,150,680 | B2 | 12/2006 | White |
| 7,150,750 | B2 | 12/2006 | Damarati |
| 7,160,309 | B2 | 1/2007 | Voss |
| 7,164,942 | B2 | 1/2007 | Avrahami |
| D536,792 | S | 2/2007 | Krueger |
| 7,184,842 | B2 | 2/2007 | Seifert |
| 7,186,255 | B2 | 3/2007 | Baynham |
| 7,186,262 | B2 | 3/2007 | Saadat |
| 7,188,627 | B2 | 3/2007 | Nelson |
| 7,191,015 | B2 | 3/2007 | Lamson |
| 7,198,595 | B2 | 4/2007 | Hegde |
| 7,201,771 | B2 | 4/2007 | Lane |
| 7,213,599 | B2 * | 5/2007 | Conrad et al. ............ 128/897 |
| 7,216,648 | B2 | 5/2007 | Nelson |
| 7,226,408 | B2 | 6/2007 | Harai |
| 7,229,417 | B2 | 6/2007 | Foerster |
| 7,229,453 | B2 | 6/2007 | Anderson |
| 7,237,553 | B2 | 7/2007 | Knudson |
| 7,237,554 | B2 | 7/2007 | Conrad et al. |
| 7,238,200 | B2 | 7/2007 | Lee |

(56) References Cited

U.S. PATENT DOCUMENTS

| | | |
|---|---|---|
| 7,247,164 B1 | 7/2007 | Ritchart |
| 7,255,109 B2 | 8/2007 | Knudson |
| 7,255,110 B2 | 8/2007 | Knudson |
| 7,285,124 B2 | 10/2007 | Foerster |
| 7,288,259 B2 | 10/2007 | Sanders |
| 7,311,103 B2 | 12/2007 | Jeppesen |
| 7,322,356 B2 | 1/2008 | Critzer |
| 7,322,993 B2 | 1/2008 | Metzger |
| 7,328,698 B2 | 2/2008 | Scarberry |
| 7,328,705 B2 | 2/2008 | Abramson |
| RE40,156 E | 3/2008 | Sharps |
| 7,337,781 B2 | 3/2008 | Vassallo |
| 7,347,812 B2 | 3/2008 | Mellier |
| 7,360,542 B2 | 4/2008 | Nelson |
| 7,361,168 B2 | 4/2008 | Makower |
| 7,363,926 B2 | 4/2008 | Pflueger |
| 7,367,340 B2 | 5/2008 | Nelson |
| 8,096,303 B2 * | 1/2012 | Dineen et al. ............. 128/848 |
| 2001/0050084 A1 | 12/2001 | Knudson |
| 2001/0050085 A1 | 12/2001 | Knudson |
| 2001/0054426 A1 | 12/2001 | Knudson |
| 2001/0054428 A1 | 12/2001 | Knudson |
| 2002/0022841 A1 | 2/2002 | Kovac |
| 2002/0035994 A1 | 3/2002 | Stevens |
| 2002/0087051 A1 | 7/2002 | Levisman |
| 2002/0107525 A1 | 8/2002 | Harari |
| 2002/0157675 A1 | 10/2002 | Clark |
| 2002/0188297 A1 | 12/2002 | Dakin et al. |
| 2003/0065402 A1 | 4/2003 | Anderson |
| 2003/0130670 A1 | 7/2003 | Anderson |
| 2003/0149445 A1 | 8/2003 | Knudson |
| 2003/0149488 A1 | 8/2003 | Metzger |
| 2004/0006339 A1 | 1/2004 | Underwood |
| 2004/0025884 A1 | 2/2004 | McKown |
| 2004/0045555 A1 | 3/2004 | Nelson et al. |
| 2004/0045556 A1 | 3/2004 | Nelson |
| 2004/0049102 A1 | 3/2004 | Nelson |
| 2004/0078054 A1 | 4/2004 | Biggs et al. |
| 2004/0122474 A1 | 6/2004 | Gellman et al. |
| 2004/0134491 A1 | 7/2004 | Pflueger |
| 2004/0138585 A1 | 7/2004 | Dematteis et al. |
| 2004/0149290 A1 | 8/2004 | Nelson |
| 2004/0172054 A1 | 9/2004 | Metzger |
| 2005/0004417 A1 | 1/2005 | Nelson |
| 2005/0092332 A1 | 5/2005 | Conrad |
| 2005/0126563 A1 | 6/2005 | van der Burg et al. |
| 2005/0241646 A1 | 11/2005 | Sotos |
| 2005/0251255 A1 | 11/2005 | Metzger |
| 2005/0267547 A1 | 12/2005 | Knudson |
| 2005/0268919 A1 | 12/2005 | Knudson |
| 2005/0268922 A1 | 12/2005 | Conrad |
| 2005/0268923 A1 | 12/2005 | Knudson |
| 2005/0274387 A1 | 12/2005 | MacKen |
| 2005/0284485 A9 | 12/2005 | Nelson |
| 2005/0287187 A1 * | 12/2005 | Mansmann ............. 424/423 |
| 2006/0005843 A9 | 1/2006 | Nelson |
| 2006/0058792 A1 | 3/2006 | Hynes |
| 2006/0060207 A1 | 3/2006 | Hegde |
| 2006/0070626 A1 | 4/2006 | Frazier |
| 2006/0090762 A1 | 5/2006 | Hegde |
| 2006/0150986 A1 | 7/2006 | Roue et al. |
| 2006/0153876 A1 | 7/2006 | Sanders |
| 2006/0157055 A1 | 7/2006 | Pflueger |
| 2006/0185673 A1 | 8/2006 | Critzer |
| 2006/0185680 A1 | 8/2006 | Bhat |
| 2006/0189971 A1 | 8/2006 | Tasto |
| 2006/0201519 A1 | 9/2006 | Hirotsuka et al. |
| 2006/0207606 A1 | 9/2006 | Roue et al. |
| 2006/0207607 A1 | 9/2006 | Hirotsuka et al. |
| 2006/0207608 A1 | 9/2006 | Hirotsuka et al. |
| 2006/0207612 A1 | 9/2006 | Jackson et al. |
| 2006/0235264 A1 | 10/2006 | Vassallo |
| 2006/0266369 A1 | 11/2006 | Atkinson |
| 2006/0266372 A1 | 11/2006 | Miller |
| 2006/0270889 A1 | 11/2006 | Nelson |
| 2006/0271059 A1 | 11/2006 | Reay-Young |
| 2006/0271060 A1 | 11/2006 | Gordon |
| 2006/0276817 A1 | 12/2006 | Vassallo |
| 2006/0276888 A1 | 12/2006 | Lee |
| 2006/0289014 A1 | 12/2006 | Purdy |
| 2006/0289015 A1 | 12/2006 | Boucher |
| 2006/0293710 A1 | 12/2006 | Foerster |
| 2007/0000497 A1 | 1/2007 | Boucher |
| 2007/0021751 A1 | 1/2007 | Reay-Young |
| 2007/0034210 A1 | 2/2007 | Paraschac |
| 2007/0079833 A1 | 4/2007 | Lamberg |
| 2007/0089756 A1 | 4/2007 | Nelson |
| 2007/0102004 A1 | 5/2007 | Nelson |
| 2007/0102010 A1 | 5/2007 | Lemperle |
| 2007/0119463 A1 | 5/2007 | Nelson |
| 2007/0137654 A1 | 6/2007 | Paraschac |
| 2007/0137655 A1 | 6/2007 | Paraschac |
| 2007/0144531 A1 | 6/2007 | Tomas |
| 2007/0144532 A1 | 6/2007 | Gillis |
| 2007/0144533 A1 | 6/2007 | Nelson |
| 2007/0144534 A1 | 6/2007 | Mery |
| 2007/0144535 A1 | 6/2007 | Hegde |
| 2007/0144539 A1 | 6/2007 | van der Burg et al. |
| 2007/0163603 A1 | 7/2007 | Sikora |
| 2007/0186936 A1 | 8/2007 | Nelson |
| 2007/0193587 A1 | 8/2007 | Boucher |
| 2007/0204866 A1 | 9/2007 | Conrad |
| 2007/0209664 A1 | 9/2007 | Paraschac |
| 2007/0209665 A1 | 9/2007 | Gillis |
| 2007/0227545 A1 | 10/2007 | Conrad |
| 2007/0233276 A1 | 10/2007 | Conrad |
| 2007/0244529 A1 | 10/2007 | Choi |
| 2007/0246052 A1 | 10/2007 | Hegde |
| 2007/0248640 A1 | 10/2007 | Karabey |
| 2007/0255172 A1 | 11/2007 | Pflueger |
| 2007/0256693 A1 | 11/2007 | Paraschac |
| 2007/0261701 A1 | 11/2007 | Sanders |
| 2007/0267027 A1 | 11/2007 | Nelson |
| 2007/0270631 A1 | 11/2007 | Nelson |
| 2007/0270632 A1 | 11/2007 | Nelson |
| 2007/0272257 A1 | 11/2007 | Nelson |
| 2007/0288057 A1 | 12/2007 | Kuhnel |
| 2007/0289600 A1 | 12/2007 | Li |
| 2007/0293727 A1 | 12/2007 | Goldfarb |
| 2007/0293946 A1 | 12/2007 | Gonzales |
| 2008/0015540 A1 | 1/2008 | Muni |
| 2008/0015594 A1 | 1/2008 | Ritchart |
| 2008/0021512 A1 | 1/2008 | Knudson |
| 2008/0023012 A1 | 1/2008 | Dineen et al. |
| 2008/0027480 A1 | 1/2008 | van der Burg et al. |
| 2008/0027560 A1 | 1/2008 | Jackson et al. |
| 2008/0033232 A1 | 2/2008 | Catanese, III |
| 2008/0033488 A1 | 2/2008 | Catanese, III |
| 2008/0035157 A1 | 2/2008 | Yan |
| 2008/0035158 A1 | 2/2008 | Pflueger |
| 2008/0035160 A1 | 2/2008 | Woodson et al. |
| 2008/0039894 A1 | 2/2008 | Catanese, III |
| 2008/0041398 A1 | 2/2008 | Hegde |
| 2008/0046022 A1 | 2/2008 | Bhat |
| 2008/0047566 A1 | 2/2008 | Hegde |
| 2008/0053461 A1 | 3/2008 | Hirotsuka et al. |
| 2008/0060660 A1 | 3/2008 | Nelson |
| 2008/0064984 A1 | 3/2008 | Pflueger |
| 2008/0065209 A1 | 3/2008 | Pflueger |
| 2008/0066764 A1 | 3/2008 | Paraschac |
| 2008/0066765 A1 | 3/2008 | Paraschac |
| 2008/0066766 A1 | 3/2008 | Paraschac |
| 2008/0066767 A1 | 3/2008 | Paraschac |
| 2008/0066769 A1 | 3/2008 | Dineen et al. |
| 2008/0081049 A1 | 4/2008 | Sanders |
| 2008/0097154 A1 | 4/2008 | Makower |
| 2008/0097239 A1 | 4/2008 | Chang |
| 2008/0097295 A1 | 4/2008 | Makower |
| 2008/0097400 A1 | 4/2008 | Chang |
| 2008/0097514 A1 | 4/2008 | Chang |
| 2008/0097515 A1 | 4/2008 | Chang |
| 2008/0097516 A1 | 4/2008 | Chang |
| 2008/0103361 A1 | 5/2008 | Makower |
| 2008/0112981 A1 | 5/2008 | Sanders |

(56) References Cited

U.S. PATENT DOCUMENTS

| | | |
|---|---|---|
| 2008/0119693 A1 | 5/2008 | Makower |
| 2008/0119875 A1 | 5/2008 | Ino |
| 2008/0125626 A1 | 5/2008 | Chang |
| 2008/0125720 A1 | 5/2008 | Kim |
| 2008/0132938 A1 | 6/2008 | Chang |
| 2008/0208265 A1 | 8/2008 | Frazier et al. |

FOREIGN PATENT DOCUMENTS

| | | |
|---|---|---|
| DE | 29614901 U1 | 10/1996 |
| DE | 20015980 U1 | 3/2001 |
| DE | 10 2005 000 702 | 7/2006 |
| DE | 60029111 T2 | 1/2007 |
| EP | 0295041 | 12/1988 |
| EP | 0702934 | 3/1996 |
| EP | 1159925 | 12/2001 |
| EP | 1216013 | 6/2002 |
| EP | 1604625 | 12/2005 |
| EP | 1239798 | 2/2007 |
| EP | 1342454 | 5/2007 |
| EP | 1797846 | 6/2007 |
| EP | 1857071 | 11/2007 |
| EP | 1867309 | 12/2007 |
| EP | 0758254 | 1/2008 |
| EP | 1339445 | 5/2008 |
| EP | 1585468 | 7/2008 |
| FR | 2880253 A | 7/1976 |
| JP | 2003265621 | 9/2003 |
| WO | WO9420040 | 9/1994 |
| WO | WO9529716 | 11/1995 |
| WO | WO9730638 | 8/1997 |
| WO | WO9900058 | 1/1999 |
| WO | WO9920339 | 4/1999 |
| WO | WO0066050 | 11/2000 |
| WO | WO0067257 | 11/2000 |
| WO | WO0119301 | 3/2001 |
| WO | WO0128457 | 4/2001 |
| WO | WO0213738 | 2/2002 |
| WO | WO02058564 | 8/2002 |
| WO | WO02062237 | 8/2002 |
| WO | WO02076341 | 10/2002 |
| WO | WO02076352 | 10/2002 |
| WO | WO02076353 | 10/2002 |
| WO | WO02076354 | 10/2002 |
| WO | WO03041612 | 5/2003 |
| WO | WO04000158 | 12/2003 |
| WO | WO2004021870 | 3/2004 |
| WO | WO2004032798 | 4/2004 |
| WO | WO2004064729 | 8/2004 |
| WO | WO2004066847 | 8/2004 |
| WO | WO2004084709 | 10/2004 |
| WO | WO2005044158 | 5/2005 |
| WO | WO2005046554 | 5/2005 |
| WO | WO2005117776 | 12/2005 |
| WO | WO2005122954 | 12/2005 |
| WO | WO2006012188 | 2/2006 |
| WO | WO2006026509 | 3/2006 |
| WO | WO2006034434 | 6/2006 |
| WO | WO2006060594 | 6/2006 |
| WO | WO2006072571 | 7/2006 |
| WO | WO2006076316 | 7/2006 |
| WO | WO2006093533 | 9/2006 |
| WO | WO2006093712 | 9/2006 |
| WO | WO2006093795 | 9/2006 |
| WO | WO2006107401 | 10/2006 |
| WO | WO2006125009 | 11/2006 |
| WO | WO2006128092 | 11/2006 |
| WO | WO2006130505 | 12/2006 |
| WO | WO2006132948 | 12/2006 |
| WO | WO2007004614 | 1/2007 |
| WO | WO2007009117 | 1/2007 |
| WO | WO2007062120 | 5/2007 |
| WO | WO2007064908 | 6/2007 |
| WO | WO2007067724 | 6/2007 |
| WO | WO2007067942 | 6/2007 |
| WO | WO2007075981 | 7/2007 |
| WO | WO2007079055 | 7/2007 |
| WO | WO2007092865 | 8/2007 |
| WO | WO2007095582 | 8/2007 |
| WO | WO2007097924 | 8/2007 |
| WO | WO2007098375 | 8/2007 |
| WO | WO2007103324 | 9/2007 |
| WO | WO2007103800 | 9/2007 |
| WO | WO2007103826 | 9/2007 |
| WO | WO2007106755 | 9/2007 |
| WO | WO2007111636 | 10/2007 |
| WO | WO2007120848 | 10/2007 |
| WO | WO2007120850 | 10/2007 |
| WO | WO2007130880 | 11/2007 |
| WO | WO2007130881 | 11/2007 |
| WO | WO2008014028 | 1/2008 |
| WO | WO2008060317 | 5/2008 |

OTHER PUBLICATIONS

Argamaso, Ravelo, M.D., *Glossopexy for Upper Airway Obstruction in Robin Sequence*. Cleft Palate-Craniofacial Journal, vol. 29, No. 3, May 1992, pp. 232-238.

Bath, A.P., et al., *Management of Upper Airway Obstruction in Pierre Robin Sequence*. The Journal of Laryngology and Otology, vol. 111, Dec. 1997, pp. 1155-1157.

Brogan, "Rapid maxillary expansion. A stable procedure for improving the nasal airway", Medical Journal of Australia, 1977, vol. 1, No. 6, pp. 167-172.

Coleman, "Suspension sutures for the treatment of obstructive sleep apnea and snoring", Otolaryngologic Clinics of North America, Apr. 1999, 32:2, 277-285.

Cozzi, D.A., et al., Recurrent Apparent Life-Threatening Event Relieved by Glossopexy. *Journal of Pediatric Surgery*, vol. 31, No. 12, Dec. 1996, pp. 1715-1718.

Deluca, "Surgically treatable causes of neonatal respiratory distress", Chilincs in Perinatology, 1978, vol. 5, No. 2, pp. 377-394.

DeRowe, Ari, M.D., et al., *Tongue-Base Suspension with a Soft Tissue-to-Bone Anchor for Obstructive Sleep Apnea: Preliminary Clinical Results of a New Minimally Invasive Technique*, Otolaryngology—Head and Neck Surgery, vol. 122, No. 1, Jan. 2000.

Douglas, Beverly, M.D., *A Further Report on the Treatment of Micrognathia with Obstruction by a Plastic Procedure*, Plastic and Reconstructive Surgery, vol. 5, No. 2, Feb. 1950, pp. 113-122.

Douglas, B., M.D., *The Treatment of Micrognathia with Obstruction by a Plastic Operation*, Department of Surgery, School of Medicine, Vanderbilt University, pp. 420-431.

Faye-Lund, H., et al., *Glossopexia—Evaluation of a new Surgical Method for Treating Obstructive Sleep Apnea Syndrome*, ACTA Otolaryngol (Stockh), 1992, Suppl. 492: pp. 46-49.

Hadley, R.C., M.D., et al., *Utilization of the Kirschner Wire in Pierre Robin Syndrome*, Plastic and Reconstructive Surgery, vol. 31, No. 6, Jun. 1963, pp. 587-596.

Havlik, "Mandibular distraction lengthening in the severely hypoplastic mandible: a problematic case with tongue aplasia", J Craniofac Surg, Nov. 1994, vol. 5, No. 5, pp. 305-310; discussion 311-2.

Hawkins, Donald B., M.D., et al., *Micrognathia and Glossoptosis in the Newborn*, Surgical Tacking of the Tongue in Small Jaw Syndromes, Clinical Pediatrics, vol. 13, No. 12, Dec. 1974, pp. 1066-1073.

Krespi, "Reconstruction after total or subtotal glossectomy", Am J Surg, Oct. 1983, vol. 146, No. 4, pp. 488-492.

Lapidot, Abraham, M.D., *A New Functional Approach to the Surgical Management of Pierre Robin Syndrome. Experimental and Clinical Report*, The Laryngoscope, A Medical Journal for Clinical and Research Contributions In: Otoloaryngology, Broncho-Esophagology, Communicative Disorders, Maxillofacial Surgery, Head and Neck Surgery, Facial Plastic and Reconstructive Surgery, vol. LXXXVI, No. 7, Jul. 1976, pp. 979-983.

Lapidot, Abraham, M.D., et al., *Fastening the Base of the Tongue Forward to the Hyoid for Relief of Respiratory Distress in Pierre Robin Syndrome*, Plastic and Reconstructive Surgery, vol. 56, No. 1, Jul. 1975, pp. 89-91.

(56) References Cited

OTHER PUBLICATIONS

Lewis, Stephen R., M.D., et al., *Fascial Slings for Tongue Stabilization in the Pierre Robin Syndrome*, Plastic and Reconstructive Surgery, vol. 42, No. 3, Sep. 1968, pp. 237-241.
Malhotra, "Postural Effects on Pharyngeal Protective Reflex Mechanisms," Sleep, vol. 27, No. 6, 2004, pp. 1105-1112.
Moore, "Mandibular lengthening by distraction for airway obstruction in Treacher-Collins syndrome", J Craniofac Surg, Feb. 1994, vol. 5, No. 1, pp. 22-25.
Moulin, "The challenge of upper airway obstruction in pediatric intensive care", Intensive Care Med., Nov. 1986, 12:412-415.
Oeconomopoulos, Chris, T., M.D., *The Value of Glossopexy in Pierre-Robin Syndrome*, The New England Journal of Medicine, vol. 262, No. 25, Jun. 23, 1960, pp. 1267-1268.
Omur, Mehmet, M.D., et al., *Tongue Base Suspenstion Combined with UPPP in Severe OSA Patients*, Otolaryngology—Head and Neck Surgery, vol. 133, No. 2, Aug. 2055, pp. 218-223.
Patton, Timothy J., M.D., Joseph H. Ogura, M.D. and Stanley E. Thawley, M.D., "Expansion Hyoidplasty," 1983 First-Place Resident Research Award: Clinical Category, vol. 92, No. 5, Oct. 1984.
PCT International Search Report for PCT-US2007-14342 mailed Sep. 18, 2008.
Piccirillo, Jay F. and Stanley E. Thawley, "Sleep-Disordered Breathing," Cummings; Otolaryngology: Head and Neck Surgery, 3rd ed., Copyright © 1998 Mosby-Year Book, Inc., Chapter 81, pp. 1546-1571.
Rama, Anil N., M.D., MPH, Shivan H. Tekwani, BS and Clete A. Kushida, M.D., Ph. D., "Sites of Obstruction in Obstructive Sleep Apenea," www.chestjournal.org, Oct. 2002.
Ramba, J., *Fixation of the Tongue Bellow Mandible in Pierre Robin Syndrome*, Department for Maxillofacial Surgery, Clinic of Paediatric Stomatology, 2$^{nd}$ Medical Faculty, Charles University, Prague, Czech Republic, ACTA Chirurgiae Plasticae 38, 2, 1996, pp. 54-56.
Ramirez, Inferior Sagittal Osteotomy with Hyoid Bone Suspension for Obese Patients with Sleep Apnea, Otolaryngology—Head and Neck Surgery, Sep. 1996, 122:953-957.
Peter Randall, M.D., "The Robin Anomalad: Micrognathia and Glossoptosis with Airway Obstruction, in Reconstructive Plastic Surgery 2241" 2241, 2d ed., W.B. Saunders Co. 1977.
Rawashdeh, Ma'amon A., BDS, MScD, FDSRCS(En), *Surgical Strategies, Transmandibular K-Wire in the Management of Airway Obstruction in Pierre Robin Sequence*, The Journal of Craniofacial Surgery, vol. 15, No. 3, May 2004, pp. 450.
Riley, Current Surgical Concepts for Treating Obstructive Sleep Apnea Syndrome:, J Oral Maxillofac Surg, Feb. 1987, 45: 149-157.
Riley, "Obstructive Sleep Apnea and Hyoid: A revised surgical procedure", Otolaryngology—Head and Neck Surgery, Dec. 1994, 11:717-721.
Riley, "Obstructive Sleep Apnea Syndrome : A review of 306 consecutively treated surgical patients", Otolaryngology—Head and Neck Surgery, Feb. 1993, 108: 117-125.
Schatten, William E., M.D., el al., *Airway Management in Patents with Pierre Robin Syndrome*, Plastic and Reconstructive Surgery, vol. 38, No 4, Oct. 1966, pp. 309-311.
Schmitz, "Hyoid Myotomy and Suspension for Obstructive Sleep Apnea Syndrome", J Oral Maxillofac Surg, Nov. 1996, 54: 1339-1345.
Shprintzen, "Pierre Robin, micrognathia, and airway obstruction: The dependency of treatment on accurate diagnosis", International Annesthesiology Clinics., 1988, vol. 26, No 1, pp. 64-71.
Sjoholm, "Mandibular advancement with dental appliances in obstructive sleep apnoea", J Oral Rehabil, vol. 21, No. 5, Sep. 1994, pp. 595-603.
Waite, "Maxillomandibular advancement surgery in 23 patients with obstructive sleep apnea syndrome", J Oral Maxillofac Surg., Dec. 1989, vol. 47, No. 12, pp. 1256-1261; discussion 1262.
M.R. Wexler, "A Dynamic Fixation of the Base of the Tongue to the Mandible Using De-epithelized Tongue Flap in the Pierre Robin Syndrome", 4 Chirurgia Plastica 297, 1979.
Robert M. Woolf, M.D., "Micrognathia and Associated Cleft Palate, 26 Plastic & Reconstructive Surgery"199, 1960.
Woodson, "Pharyngeal Suspension suture with Response bone screw for obstructive sleep apnea", Otolaryngology—Head and Neck Surgery, Mar. 1999, 122:395-401.
Yin, "Mandibular advancement for the treatment of micrognathia with obstructive sleep apnea", Zhonghua Zhueng Xing Shao Shang Wai Ke Za Zhi, vol. 10, No. 4, Jul. 1994, pp. 265-269.

\* cited by examiner

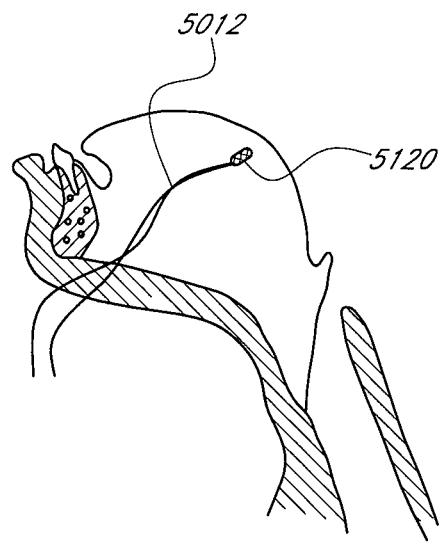
FIG. 10A
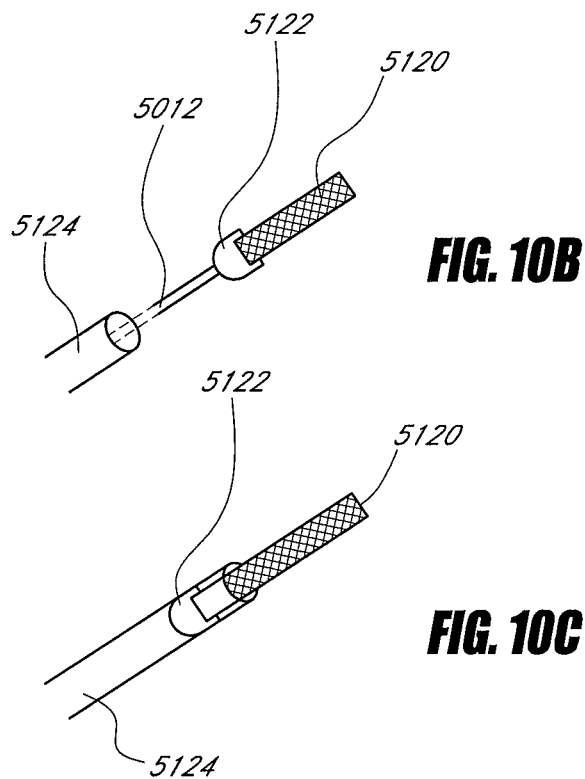
FIG. 10B
FIG. 10C

AIRWAY IMPLANTS AND METHODS AND DEVICES FOR INSERTION AND RETRIEVAL

The present application is a divisional application and claims priority under 35 U.S.C. §119(e) of U.S. patent application Ser. No. 11/835,931, filed on Aug. 8, 2007, which claims priority under 35 U.S.C. §119(e) to U.S. Provisional Application No. 60/836,579 filed on Aug. 8, 2006. The present application also claims priority under 35 U.S.C. §120 as a continuation-in-part of U.S. patent application Ser. No. 11/349,044, filed Feb. 7, 2006, which claims priority to U.S. Provisional Application Nos. 60/650,867 filed Feb. 8, 2005 and 60/726,028 filed Oct. 12, 2005. All of the priority applications are hereby incorporated by reference in their entirety.

BACKGROUND

Certain embodiments of the present invention are related to methods and devices for the treatment of airway obstruction, such as, for example, obstructive sleep apnea, and devices and methods that facilitate insertion and retrieval of the same.

FIELD OF THE INVENTION

This invention relates generally to a system and method for treating upper airway obstruction, sleep disordered breathing, upper airway resistance syndrome and snoring by manipulating the structures of the oropharynx, including the tongue.

DESCRIPTION OF THE RELATED ART

Respiratory disorders during sleep are recognized as a common disorder with significant clinical consequences. During the various stages of sleep, the human body exhibits different patterns of brain and muscle activity. In particular, the REM sleep stage is associated with reduced or irregular ventilatory responses to chemical and mechanical stimuli and a significant degree of muscle inhibition. This muscle inhibition may lead to relaxation of certain muscle groups, including but not limited to muscles that maintain the patency of the upper airways, and create a risk of airway obstruction during sleep. Because muscle relaxation narrows the lumen of the airway, greater inspiratory effort may be required to overcome airway resistance. This increased inspiratory effort paradoxically increases the degree of airway resistance and obstruction through a Bernoulli effect on the flaccid pharyngeal walls during REM sleep.

Obstructive Sleep Apnea (OSA) is a sleep disorder that affects up to 2 to 4% of the population in the United States. OSA is characterized by an intermittent cessation of airflow in the presence of continued inspiratory effort. When these obstructive episodes occur, an affected person will transiently arouse, regain muscle tone and reopen the airway. Because these arousal episodes typically occur 10 to 60 times per night, sleep fragmentation occurs which produces excessive daytime sleepiness. Some patients with OSA experience over 100 transient arousal episodes per hour.

In addition to sleep disruption, OSA may also lead to cardiovascular and pulmonary disease. Apnea episodes of 60 seconds or more have been shown to decrease the partial pressure of oxygen in the lung alveoli by as much as 35 to 50 mm Hg. Some studies suggest that increased catecholamine release in the body due to the low oxygen saturation causes increases in systemic arterial blood pressure, which in turn causes left ventricular hypertrophy and eventually left heart failure. OSA is also associated with pulmonary hypertension, which can result in right heart failure.

Radiographic studies have shown that the site of obstruction in OSA is isolated generally to the supralaryngeal airway, but the particular site of obstruction varies with each person and multiple sites may be involved. A small percentage of patients with OSA have obstructions in the nasopharynx caused by deviated septums or enlarged turbinates. These obstructions may be treated with septoplasty or turbinate reduction procedures, respectively. More commonly, the oropharynx and the hypopharynx are implicated as sites of obstruction in OSA. Some studies have reported that the occlusion begins with the tongue falling back in an anterior-posterior direction (A-P) to contact with the soft palate and posterior pharyngeal wall, followed by further occlusion of the lower pharyngeal airway in the hypopharynx. This etiology is consistent with the physical findings associated with OSA, including a large base of tongue, a large soft palate, shallow palatal arch and a narrow mandibular arch. Other studies, however, have suggested that increased compliance of the lateral walls of the pharynx contributes to airway collapse. In the hypopharynx, radiographic studies have reported that hypopharyngeal collapse is frequently caused by lateral narrowing of the pharyngeal airway, rather than narrowing in the A-P direction.

OSA is generally diagnosed by performing overnight polysomnography in a sleep laboratory. Polysomnography typically includes electroencephalography to measure the stages of sleep, an electro-oculogram to measure rapid eye movements, monitoring of respiratory effort through intercostal electromyography or piezoelectric belts, electrocardiograms to monitor for arrhythmias, measurement of nasal and/or oral airflow and pulse oximetry to measure oxygen saturation of the blood.

Following the diagnosis of OSA, some patients are prescribed weight loss programs as part of their treatment plan, because of the association between obesity and OSA. Weight loss may reduce the frequency of apnea in some patients, but weight loss and other behavioral changes are difficult to achieve and maintain. Therefore, other modalities have also been used in the treatment of OSA, including pharmaceuticals, non-invasive devices and surgery.

Among the pharmaceutical treatments, respiratory stimulants and drugs that reduce REM sleep have been tried in OSA. Progesterone, theophylline and acetozolamide have been used as respiratory stimulants, but each drug is associated with significant side effects and their efficacy in OSA is not well studied. Protriptyline, a tricyclic antidepressant that reduces the amount of REM sleep, has been shown to decrease the frequency of apnea episodes in severe OSA, but is associated with anti-cholinergic side effects such as impotence, dry mouth, urinary retention and constipation.

Other modalities are directed at maintaining airway patency during sleep. Oral appliances aimed at changing the position of the soft palate, jaw or tongue are available, but patient discomfort and low compliance have limited their use. Continuous Positive Airway Pressure (CPAP) devices are often used as first-line treatments for OSA. These devices use a sealed mask which produce airflow at pressures of 5 to 15 cm of water and act to maintain positive air pressure within the pharyngeal airway and thereby maintain airway patency. Although CPAP is effective in treating OSA, patient compliance with these devices is low for several reasons. Sleeping with a sealed nasal mask is uncomfortable for patients. Smaller sealed nasal masks may be more comfortable to patients but are ineffective in patients who sleep with their mouths open, as the air pressure will enter the nasopharynx and then exit the oropharynx. CPAP also causes dry nasal passages and congestion.

Surgical treatments for OSA avoid issues with patient compliance and are useful for patients who fail conservative treatment. One surgery used for OSA is uvulopalatopharyngoplasty (UPPP). UPPP attempts to improve airway patency in the oropharynx by eliminating the structures that contact the tongue during sleep. This surgery involves removal of the uvula and a portion of the soft palate, along with the tonsils and portions of the tonsillar pillars. Although snoring is reduced in a majority of patients who undergo UPPP, the percentage of patients who experience reduced frequency of apnea episodes or improved oxygen saturation is substantially lower. Postoperatively, many patients that have undergone UPPP continue to exhibit oropharyngeal obstruction or concomitant hypopharyngeal obstruction. Nonresponders often have physical findings of a large base of tongue, an omega-shaped epiglottis and redundant aryepiglottic folds. UPPP is not a treatment directed at these structures. UPPP also exposes patients to the risks of general anesthesia and postoperative swelling of the airway that will require a tracheostomy. Excessive tissue removal may also cause velopharyngeal insufficiency where food and liquids enter into the nasopharynx during swallowing.

Laser-assisted uvulopalatopharyngoplasty (LAUP) is a similar procedure to UPPP that uses a CO2 laser to remove the uvula and portions of the soft palate, but the tonsils and the lateral pharyngeal walls are not removed.

For patients who fail UPPP or LAUP, other surgical treatments are available but these surgeries entail significantly higher risks of morbidity and mortality. In genioglossal advancement with hyoid myotomy (GAHM), an antero-inferior portion of the mandible, which includes the attachment point of the tongue musculature, is repositioned forward and in theory will pull the tongue forward and increase airway diameter. The muscles attached to the inferior hyoid bone are severed to allow the hyoid bone to move superiorly and anteriorly. Repositioning of the hyoid bone expands the retrolingual airspace by advancing the epiglottis and tongue base anteriorly. The hyoid bone is held in its new position by attaching to the mandible using fascia. Variants of this procedure attach the hyoid bone inferiorly to the thyroid cartilage.

A laser midline glossectomy (LMG) has also been tried in some patients who have failed UPPP and who exhibit hypopharyngeal collapse on radiographic studies. In this surgery, a laser is used to resect the midline portion of the base of the tongue. This involves significant morbidity and has shown only limited effectiveness.

In some patients with craniofacial abnormalities that include a receding mandible, mandibular or maxillomandibular advancement surgeries may be indicated for treatment of OSA. These patients are predisposed to OSA because the posterior mandible position produces posterior tongue displacement that causes airway obstruction. In a mandibular advancement procedure, the mandible is cut bilaterally posterior to the last molar and advanced forward approximately 10 to 14 mm. Bone grafts are used to bridge the bone gap and the newly positioned mandible is wire fixated to the maxilla until healing occurs. Mandibular advancement may be combined with a Le Fort I maxillary osteotomy procedure to correct associated dental or facial abnormalities. These procedures have a high morbidity and are indicated only in refractory cases of OSA.

Experimental procedures described in the clinical literature for OSA include the volumetric radiofrequency tissue ablation and hyoidplasty, where the hyoid bone is cut into several segments and attached to a brace that widens the angle of the U-shaped hyoid bone. The latter procedure has been used in dogs to increase the pharyngeal airway lumen at the level of the hyoid bone. The canine hyoid bone, however, is unlike a human hyoid bone because the canine hyoid bone comprises nine separate and jointed bones, while the human hyoid bone comprises five bones that are typically fused together.

Notwithstanding the foregoing, there remains a need for improved methods and devices for treating obstructive sleep apnea.

SUMMARY OF THE INVENTION

Methods and devices for manipulating tissue are provided. A tissue-tensioner is used to tension a region of tissue. The tissue tensioner is used to engage certain tissue of the body and apply tension to those tissues.

In further embodiments, methods and devices are disclosed for manipulating the tongue, or alternatively the soft palate. A tissue engaging structure can be positioned on the tongue, and the device is manipulated to displace at least a portion of the posterior tongue in an anterior or lateral direction, or to alter the tissue tension or compliance of the tongue.

In one embodiment, disclosed is a tissue tensioner for treating a condition of a patient's airway, said tissue tensioner including an elongate flexible tether having a first end and a second end; a bone anchor configured to be connected to a patient's mandible; and a tissue ingrowth implant configured to be implanted in a patient's tongue. The tissue ingrowth implant can be connected to the second end of the tether. The tissue tensioner can also include an adjustment mechanism configured to be held by the bone anchor adjacent the patient's mandible. The adjustment mechanism can be configured to receive the first end of the tether, as well as configured to adjust tension in the flexible tether between the patient's mandible and the patient's tongue. In some embodiments the elongate member can include either an active variable length tether or a coating tending to cause tissue ingrowth. The adjustment mechanism can include a rotational assembly such as a spool.

In one embodiment, disclosed is a tissue tensioner for treating a condition of a patient's airway, the tensioner including an elongate flexible tension member; a first portion of the tension member configured to be secured relative to a body tissue; and a second portion of the tension member including a tissue ingrowth material configured to be secured to a portion of a tongue; and an adjustment mechanism configured to adjust tension in the tension member between the body tissue and said portion of the tongue. In some embodiments the first portion of the tension member can be connected to either a bone anchor or a tissue anchor. In some embodiments the tissue ingrowth material is a single strand of woven material which may be partially covered by a cap element. The cap element can be radiopaque. The tension member can be beaded in some embodiments.

In one embodiment, a method for treating airway obstruction is disclosed. The method includes the steps of placing a tissue tensioner within a patient's tongue, the tensioner including a flexible elongate tension member having a first portion configured to be secured relative to a body tissue and a second portion that is connected to a tissue ingrowth material; an adjustment mechanism configured to adjust tension in the tension member between the body tissue and the tissue ingrowth material; securing the first portion relative to a body tissue and implanting the tissue ingrowth material within a portion of the tongue; and adjusting the tension of the tension member by manipulating the adjustment mechanism. In some embodiments the first portion is either secured relative to a patient's mandible using a bone anchor, or secured to tongue tissue using a tissue anchor. In some embodiments, the tissue ingrowth implant includes a single strand of woven material.

In another embodiment, disclosed is a tissue tensioner for treating a condition of a patient's airway, including an elongate flexible tension member comprising a first portion and a second portion; the first portion of the tension member being securable relative to a body tissue; the second portion being connected to a tissue ingrowth material; and means for adjusting the tension between the tissue ingrowth material and the body tissue. In some embodiments, the first portion of the tension member can be configured to be connected to either a bone anchor or a tissue anchor.

In another embodiment, disclosed is a tissue tensioner for treating a condition of a patient's airway that includes a flexible elongate tension member having a first portion and a second portion. The first portion can be securable relative to a body tissue, and the second portion can be connected to an implant including a single woven strand and configured to be implanted in a patient's tongue. A cap element can cover a portion of the woven implant.

In one embodiment, disclosed is a method for treating airway obstruction including the steps of deploying a tissue tensioner into a patient's tongue, the tissue tensioner including a flexible elongate tension member having a first portion secured relative to a body tissue and a second portion including a single strand woven implant that can be implanted in a patient's tongue. In some embodiments, the method also includes the step of removing the tissue tensioner from the patient by pulling on the single strand with sufficient force such that the woven implant unravels. The first portion may be secured either relative to the patient's mandible or within the patient's tongue.

In one embodiment, disclosed is a tissue tensioner for treating a condition of a patient's airway including a flexible elongate elastic member having a first portion and a second portion, wherein the first portion is configured to be secured relative to a body tissue and the second portion is connected to a tissue ingrowth material; and a locking bar releasably attached to the first portion and the second portion. The locking bar can be configured to prevent migration of the first portion relative to the second portion.

In one embodiment, disclosed is a method for treating a condition of a patient's airway, the method including the step of positioning a tissue tensioner within a patient. The tissue tensioner can include a flexible, elongate elastic member having a first portion secured relative to a body tissue and a second portion comprising a tissue ingrowth material implanted in a portion of the tongue. A locking bar is preferably releasably attached to the first portion and the second portion to prevent migration of the first portion with respect to the second portion. The locking bar can be manually pulled out to allow migration of the first portion with respect to the second portion.

In yet another embodiment, disclosed is a method for removing a tissue tensioner including the steps of providing a tissue tensioner, the tissue tensioner comprising a batten implant connected to a flexible tether; threading the flexible tether through a dilator; advancing the dilator over the flexible tether through tissue to the batten implant; advancing a cannula over dilator and over the implant; and removing the batten implant, the cannula, and the dilator. In some embodiments, at least a portion of the tissue ingrowth material is covered by a cap element.

In one embodiment, disclosed is a method for treating a condition of a patient's airway, including the steps of passing a first tension member through a patient's genioglossus muscle exiting the dorsum lateral to a midline of the patient's tongue creating a first exit hole; passing a second tension member through the patient's genioglossus muscle exiting the dorsum lateral to the midline of the patient's tongue creating a second exit hole; passing a sling element under the tongue surface though the first exit hole and the second exit hole; attaching the first tension member to a first portion of the sling; attaching the second tension member to a second portion of the sling; and securing first and second tension members relative to body tissue. In some embodiments the first and second tension members are secured to bone anchors.

In another embodiment, disclosed is a method for treating airway obstruction including the steps of placing a tissue tensioner within a patient's oral cavity, the tensioner including a flexible elongate tension member having a first portion configured to be secured relative to a body tissue and a second portion that is connected to a tissue ingrowth material; an adjustment mechanism configured to adjust tension in the tension member between the body tissue and the tissue ingrowth material; securing the first portion relative to a body tissue and implanting the tissue ingrowth material within a portion of the patient's soft palate; and adjusting the tension of the tension member by manipulating the adjustment mechanism. In some embodiments the first portion is secured relative to a patient's hard palate.

In still another embodiment, disclosed is a tissue tensioner for treating a condition of an airway, the tissue tensioner including: an elongate flexible tension member, a first portion of the tension member connected to a first tissue ingrowth material and a second portion of the tension member connected to a second tissue ingrowth material; and an adjustment mechanism configured to adjust tension in the tension member between the first tissue ingrowth material and the second tissue ingrowth material. In some embodiments the first tissue ingrowth material is implanted in a first body tissue and the second tissue ingrowth material is implanted in a second body tissue.

In yet another embodiment, disclosed is a method for treating airway obstruction, the method including placing a tissue tensioner within the tongue, the tensioner including a flexible elongate tension member having a first portion connected to a first tissue ingrowth material and a second portion connected to a second tissue ingrowth material; implanting the first tissue ingrowth material in a first portion of the tongue and implanting the second tissue ingrowth material in a second portion of the tongue; and adjusting the tension or length of the tension member by manipulating an adjustment mechanism configured to adjust tension in the tension member between the first tissue ingrowth material and the second tissue ingrowth material.

In another embodiment, disclosed is a tissue tensioner for treating a condition of a patient's airway, the tissue tensioner including an elongate flexible tension member, a first portion of the tension member including a tissue anchor configured to be secured to a first portion of a patient's tongue and a second portion of the tension member including a tissue ingrowth material configured to be secured to a second portion of the patient's tongue. The tissue anchor may include a fishbone anchor that has a plurality of barbs extending radially from the tension member.

In another embodiment, disclosed is a method for treating airway obstruction including placing a tissue implant within a patient's tongue or palate, the tissue implant comprising a multiple-pronged stiffening element; and expanding the stiffening element within the tongue or palate to stretch tissue laterally. The stiffening implant may have at least one, two, three, four, five, or more prongs.

BRIEF DESCRIPTION OF THE DRAWINGS

FIGS. 10A-C illustrate a recapture/removal tool for a batten-style implant, according to one embodiment of the invention.

DETAILED DESCRIPTION OF THE PREFERRED EMBODIMENTS

Causes of airway obstruction include but are not limited to obstructive sleep apnea, snoring and congenital disorders such as Pierre-Robin syndrome. Disclosed herein are various embodiments of devices or implants and methods for treating causes of airway obstruction. Embodiments described herein relate to, for example, adjustability, tethers, and anchors of those implants to treat said conditions. Also disclosed herein are methods and devices for deployment and retrieval of the implants disclosed. Some of such devices and methods are further described in co-pending application Ser. No. 11/349,040, filed Feb. 7, 2006, as well as in U.S. Patent Publication Nos. 2005/0092332 and 2005/0092334 to Conrad et al. (herein, "Conrad"), which are hereby incorporated by reference in their entirety. References to figures disclosed in Conrad herein refer to Publication No. 2005/0092334. In various embodiments, Conrad discloses implants and methods of using the implants to alter the geometry and position of the tongue and soft palate. Embodiments disclosed herein may also be adapted for use with the PILLAR® system of Restore Medical (St. Paul, Minn.).

U.S. patent application Ser. No. 11/349,040, filed Feb. 7, 2006 and published Sep. 14, 2006 as U.S. Patent Pub. No. 2006-0201519 A1 ("Frazier '519 publication"); U.S. Provisional Patent Application No. 60/813,230, filed Jun. 13, 2006 ("'230 provisional application"); U.S. Provisional Patent Application No. 60/813,285, filed Jun. 13, 2006 ("'285 provisional application); U.S. Patent Application No. 60/813,058, filed Jun. 13, 2006 ("'058 provisional application"); U.S. Patent Publication No. 2005/0092334 to Conrad et al ("Conrad"); U.S. Pat. No. 6,250,307 to Conrad et al. ("Conrad '307"); U.S. patent application Ser. No. 11/762,642 filed Jun. 13, 2007 ("Dineen '642 application"); U.S. patent application Ser. No. 11/762,752 filed Jun. 13, 2007 ("'Hirotsuka '752 application"); and U.S. patent application Ser. No. 11/762,652 filed Jun. 13, 2007 ("Jackson '652 application") are all incorporated by reference herein in their entirety.

Figure 1:
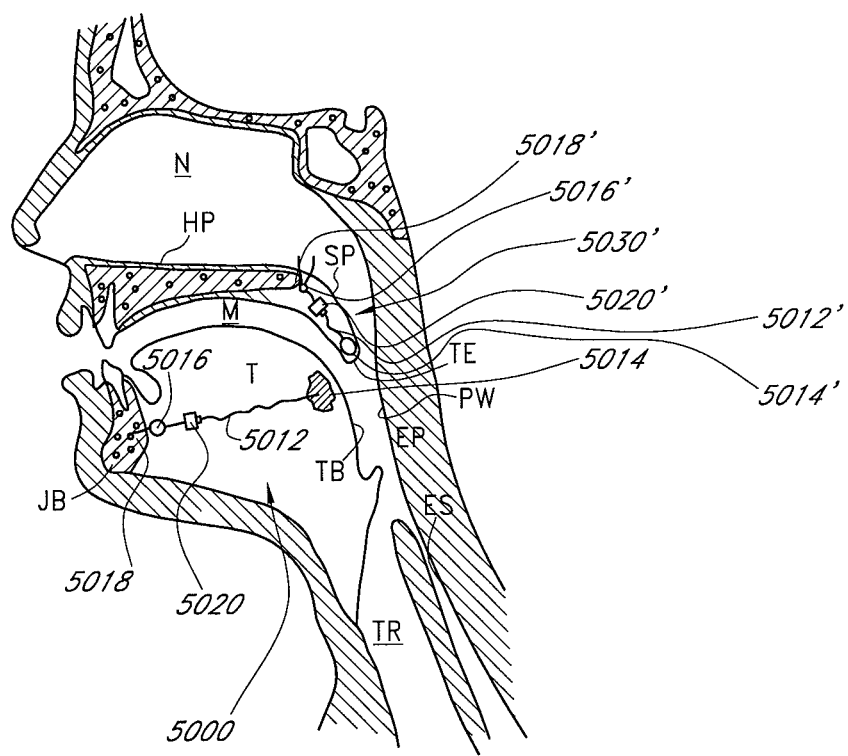
FIG. 1 illustrates tongue and soft palate implants including adjustment elements to adjust the tension of a tether, according to one embodiment of the invention.
Figure 3:
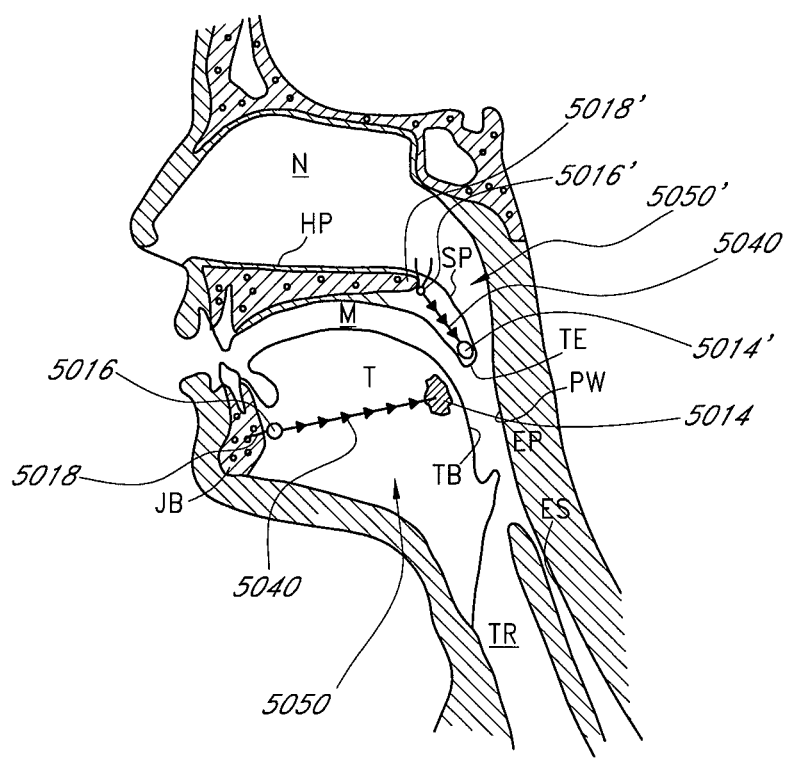
FIG. 3 shows tongue and soft palate implants comprising tethers with a beaded shape, according to one embodiment of the invention.

Conrad discloses various methods and apparatuses for treating a condition of a patient's airway. FIG. 1 of Conrad illustrates an implant 10 that may be completely implanted within the tongue T, or alternatively, the soft palate SP. The implant 10 comprises an elongated member 12 having a tissue in-growth end 14 and a static end 16. In some embodiments, as shown in FIG. 3 of Conrad, the elongated member 12a may be resilient, e.g., in the form of a spring member which may be stretched to create a bias urging tissue in-growth 14a and static ends 16a of the spring together. In some embodiments, the implant may comprise a bioresorbable material 20 positioned between the tissue-engaging end 14a of the elongated member 12a and an anchor 18a. The tissue in-growth end 14a may be a tissue growth inducing material (e.g., felt or PET) to induce growth of tissue into the end to secure the end to surrounding tissue following implantation. An anchor 18a, positioned proximally (e.g., a threaded eye-bolt) is secured to the mandible JB for tongue implants, and the hard palate HP for soft palate SP implants 10'. The static end 16 of the elongated member 12 is secured to the anchor 18. The tissue in-growth end 14 is placed in the tongue T near the tongue base TB. A surgeon adjusts the tension of the suture 12, causing the tongue base TB to be advanced toward the mandible JB thereby placing the tissue of the tongue T in compression. The surgeon may tie off the static end 16 at the anchor 18 retaining the tissue of the tongue T under tension. Other anatomical structures shown include the trachea TR, epiglottis EP, esophagus ES, pharyngeal wall PW, trailing end of the soft palate TE, mouth M, and nasal cavity N.

In some embodiments, as shown in FIG. 11 of Conrad, tissue in-growth material 118 deployed proximally acts as an embedded anchor and eliminates the need for placement of an anchor in the mandible JB.

Adjustment Mechanisms

As noted above, FIG. 1 of Conrad illustrates an implant 10 that includes an elongated member 12 (also referred herein as a tether or a tension member) having a tissue in-growth end 14 and a static end 16. In some embodiments, as shown in FIG. 3 of Conrad, the elongated member may be resilient, e.g., in the form of a spring member 12a which may be stretched to create a bias urging tissue in-growth 14a and static ends 16a of the spring 12a together. In some embodiments, the implant 10a may comprise a bioresorbable material 20 positioned between the tissue-engaging end 14a of the elongated member 12a and an anchor 18a. The tissue in-growth end 14a may be a tissue growth inducing material (e.g., felt or PET) to induce growth of tissue into the end to secure the end to surrounding tissue following implantation.

In some embodiments, the devices discussed above can also include one or more adjustment elements, for example, one or more adjustment elements selected from those described in the Frazier '519 publication (e.g., those illustrated in FIGS. 61A-K of the Frazier '519 publication), the '230 provisional application (e.g., those illustrated in FIGS. 73-108 of the '230 provisional application), or the Dineen '642 application (e.g., those illustrated in FIGS. 73-98 of the Dineen '642 application). Adjustment elements can advantageously allow for adjusting the tension of the elongated member disclosed in Conrad after implantation of the tongue or palatal suspension system. A tongue or palatal remodeling system, device, and/or method for treating a patient with breathing problems that can be adjusted either before, during and/or after the initial implantation procedure may be better tolerated and less prone to treatment failure. For example, by being able to adjust the tension or bias of the elongated member disclosed in Conrad by methods other than by cutting and re-tying the elongated member at times other than during implantation, migration, extrusion, and/or dysphagia may be avoided or corrected.

For example, in one embodiment of the invention, shown schematically in FIG. 1 herein, the improved tongue suspension system 5020 includes one or more spools or rotation assemblies 5020, such as a spool assembly illustrated in FIGS. 61A to 61I of the Frazier '519 publication, for adjusting the tension of an elongated member 5012 between the mandibular anchor 5018 (attached to static end 5016 of the system) and the tissue in-growth end 5014 of the elongated member 5012, such as one disclosed in Conrad. A improved palatal suspension system 5030 is also shown in FIG. 1 that can be similar to the tongue suspension system, including one or more spools or rotation assemblies 5020' for adjusting the tension of an elongated member 5012' between a bone or hard palate anchor 5018' (attached to static end 5016' of the system) and the tissue in-growth end 5014 of the elongated member 5102' attached to the soft palate. In some embodiments, the elongated member may be configured to adjust the tension between a soft tissue anchor and the tissue ingrowth end.

Securement Assemblies

In some embodiments, the aforementioned implants may include one or more securement mechanisms selected from those disclosed in disclosed in the Frazier '519 publication, (e.g., securement mechanisms illustrated in FIGS. 40-51 of the Frazier '519 publication) which may be configured for use a system such as the one disclosed in Conrad. For example, the bone anchor disclosed in Conrad may be replaced by a securement mechanism as disclosed in the Frazier '519 publication. The securement mechanism may be configured to hold the elongated member disclosed in Conrad or one or more tethers disclosed in, for example, the Frazier '519 publication or the Hirotsuka '752 application.

In one embodiment, illustrated schematically in FIG. 2, the tongue or soft palate implant such as one disclosed in Conrad includes a bone anchor 186 with a clamping interface 188 for retaining tethers 28, as illustrated in connection with FIGS. 40A-C of the Frazier '519 publication. The clamping interface 188 comprises two opposing surfaces 190, 192 or structures that are adapted to provide a frictional or mechanical interface with tethers 28 or other elongate members inserted within the clamping interface 188. The clamping interface 188 has an open configuration depicted in FIGS. 40A-C of the Frazier '519 publication to allow positioning of one or more tethers 28 within the interface 188 and a closed configuration shown for retaining the tethers 28. The closed configuration may be achieved by crimping the two opposing surfaces 190, 192 or by further structures of the clamping interface, such as complementary clasps or clip structures to fix the opposing surfaces 190, 192 together. As shown in FIG. 40C of the Frazier '519 publication, the clamping interface 188 may further comprise complementary indentations 194 and protrusions 196 to further enhance the frictional resistance of the interface in the closed configuration. The opposing surfaces or structures of the clamping interface may also be configured with frictional surfaces that are well known in the art through the use of various materials, surface treatments or configurations. Frictional surface configurations may also include cross hatched surfaces or irregular porous surfaces.

Tethers

As described above, Conrad teaches an elongated member having a tissue in-growth end and a static end. In some embodiments, as shown in FIG. 3 of Conrad, the elongated member 12a may be resilient, e.g., in the form of a spring member 12a which may be stretched to create a bias urging tissue in-growth 14a and static 16a ends of the spring together. An elongated member, such as one disclosed in Conrad may include any one of various tethers disclosed in the Frazier '519 publication (e.g., those illustrated in FIGS. 27-38 of the Frazier '519 publication), the '285 provisional application (e.g., those illustrated in FIGS. 73-84 of the '285 provisional application), or the Hirotsuka '752 application (e.g., those illustrated in FIGS. 73-80C of the Hirotsuka '752 application), and configured for use with the aforementioned Conrad tongue or palatal implants. A tether with elastic properties or comprising structures that provide a length/tension relationship may be preferred in some instances. A tether capable of lengthening in response to increased load or tension may be optimized to provide sufficient bias to reduce the effects of oropharyngeal occlusion while providing a more physiologic range of tongue or soft palate motion than that produced by fixed length tethers. Fixed length glossoplasty or suspension of the tongue may be the cause of odynophagia, dysphagia and deglutition problems seen with existing tongue remodeling devices, but the current invention is not limited to this purpose. A tether with elastomeric properties may be provided by using materials such as but not limited to urethane or silicone. One skilled in the art can select the particular material, tether length, diameter, cross-sectional shape and other features based upon the desired effect, tolerances, and the particular patient's anatomical characteristics. Other materials that may comprise the tether include but are not limited to Nitinol, spring steel, tantalum, polyethylene, polyester, silk, polypropylene, polyolefin or a combination thereof.

Other tether configurations that may be used include passive and active variable length or bias structures such as braided or woven structures, electropolymers, springs, coils, magnets or solenoids. Thus, in some of the embodiments, the tether configuration may actively change in length or configuration resulting from the application of external energy or force such as electrical current or magnets. These active tether configurations may be further configured with local or distal sensor components that may modulate the activity of the external energy or force acting on the active tether. The modulation may be influenced or triggered by detection of diaphragm movement or depolarization activity, nerve depolarization, pressure changes and/mechanical contact in the airway.

The tether may also be covered by a lubricious biocompatible coating. In another embodiment, the tether comprises a bioabsorbable coating that may cause scar or connective tissue formation about the tether. Scar tissue formation may further enhance the effect of the glossoplasty implant by tightening the tongue tissue (or similarly with regard to a palatal implant) and/or to resist migration of the implant.

In some embodiments, a tether of a tissue engaging member may be configured with one or more structures or surfaces capable of engaging at least a portion of the tissue surrounding the tether so that an anchor is not required, or to distribute the tissue engagement. In still other embodiments, the tissue engaging member may comprise multiple anchors and multiple tethers arranged in a serial or branching fashion.

FIG. 3 illustrates an embodiment of tongue 5050 and soft tissue 5050' implants, both comprising a beaded tether 5040, 5040', as disclosed in, for example, the Frazier '519 publication, the '285 provisional application, and the Hirotsuka '752 application. The beaded tether 5040, 5040' may advantageously promote tissue in-growth and better tension the tongue 5050 or soft palate 5050' suspension system. In other embodiments, one or more tethers selected from the tethers disclosed in the Frazier '519 publication, the '285 provisional application, or the Hirotsuka '752 application replace the elongated member disclosed in Conrad.

Figure 4C:
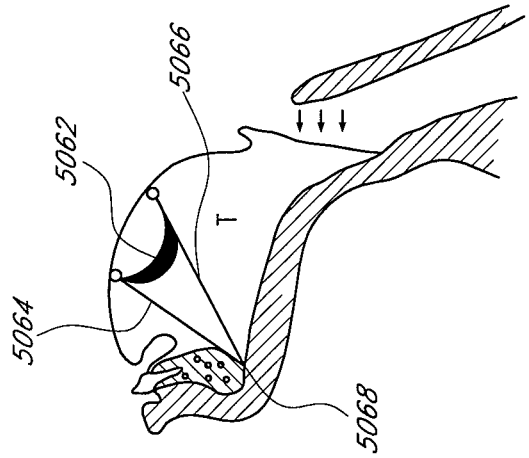
FIGS. 4A-C depict a tongue suspension system comprising a multi-piece sling, according to one embodiment of the invention.
Figure 4B:
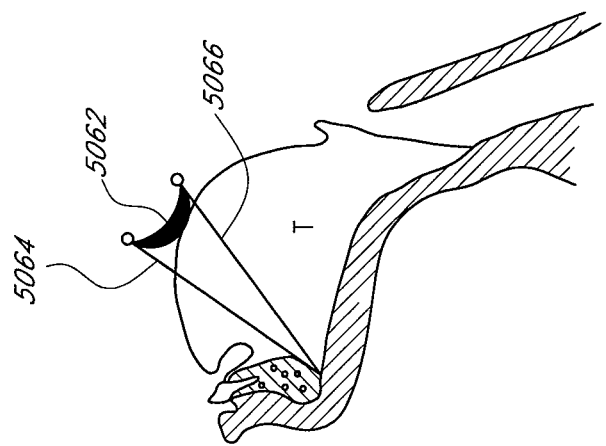
Figure 4A:
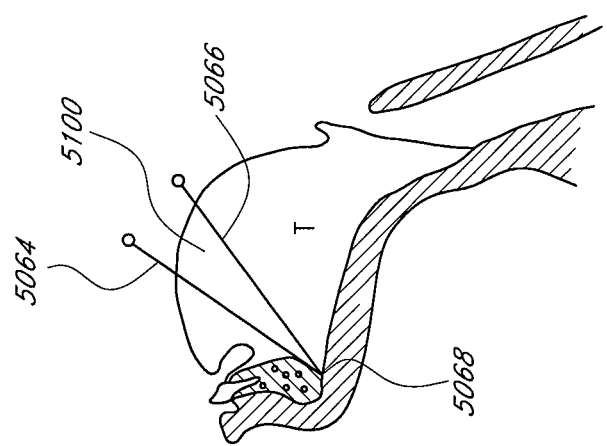

As illustrated in FIGS. 4A-4C, in one embodiment, an improved tongue suspension system 5060 comprises a tether further comprising one or more "sling" elements 5062 on a tongue or palate-based implant system such as disclosed in Conrad. The sling element 5062 may comprise, for example, a batten of porous fabric, woven material, a large diameter suture, braid, band, and the like. The sling element 5062 may be operably connected to, or replace the elongated member disclosed in Conrad. In some embodiments, the sling element 5062 comprises a central lumen configured to receive one or more sutures within the lumen. The sling element 5062 may alleviate trauma during installation of the tongue suspension system 5060 because the enlarged suture portion 5062 need not be passed through the entire tongue T. The sling 5062 can also advantageously increase anchoring surface area in the tongue T and prevent undesired migration of the elongated member.

A method of deploying an improved tongue suspension system 5060 comprising a sling element 5062 is disclosed herein, and illustrated in FIGS. 4A-4C. The method comprises the step of passing a first elongated member 5064 through the genioglossus muscle 5100 exiting the dorsum lateral to the midline. Next, a second elongated member 5066 is passed through the genioglossus muscle 5100 exiting the dorsum lateral to the midline on the contralateral side. Next, a sling element 5062 is passed under the tongue T surface between exit holes created from the passing of the first 5064 and second 5066 elongated members through the genioglossus muscle 5100. Then, elongated members 5064, 5066, such as sutures are attached to each end of the sling element 5062. In some embodiments with a sling element 5062 that further include a lumen, the portion of the elongated member within the sling element may be secured within the lumen of the sling element 5062. The elongated members 5064, 5066 outside of the sling element may then be attached to the bone anchor 5068. In another embodiment, the sling element 5062 is formed during the procedure by passing a plurality of sutures transversely through the tongue along different pathways. The ends of the sutures located to each side of the midline tongue are then joined together to form the ends of the sling element. The in situ formed sling element can then be attached to the first and second sutures as described above.

Tissue Engagement

As described above, Conrad teaches an elongated member having a tissue in-growth end. In some embodiments, as described with reference to FIG. 11 of Conrad, the elongated member 12 has two tissue in-growth ends (e.g., felt or PET); a proximal in-growth end 118 acting as an embedded anchor eliminating the need for placing an anchor in the mandible, and a distal in-growth end 14 for tensioning the tongue suspension system. In one embodiment of the present invention, a tongue suspension system comprises an implant with one or more anchors selected from the anchors disclosed in the Frazier '519 publication (e.g., as illustrated in FIGS. 7-26 of the Frazier '519 publication), the '058 provisional application (e.g., as illustrated in FIGS. 73-112 of the '058 provisional application), or the Jackson '652 application replacing the one or more tissue in-growth ends of a tongue or palatal implant disclosed in Conrad. The anchors can advantageously improve tongue or palatal suspension by providing a greater surface area and resistance to migration of the implant. For example, in one embodiment as illustrated schematically in FIG. 5 herein, the tissue in-growth ends may comprise double-ended anchors 5080 as illustrated, for example, in FIGS. 86-112 of the '058 provisional application, or the anchors of the Jackson '652 application. The anchor may be operably connected to the elongated member as disclosed in Conrad, or a tether as disclosed in the Frazier '519 application, '058 provisional application, or the Jackson '652 application as noted above. Other tissue ingrowth materials that may be used include polypropylene, polytetrafluoroethylenes, polyurethanes, polyesters, ceramics, porous metals or combinations thereof. In some embodiments, bioglues may be used to facilitate tissue adhesion to the implant. Bioglues may be injected at the implantation site or provided as a coating on the implant. A bioglue coating may provided at the point of manufacture or the point of service. In some embodiments, a tongue suspension system may include a first tissue ingrowth portion and a second tissue ingrowth portion, connected by a flexible elongate tether. The length and/or tension of the tether can be adjusted using an adjustment mechanism described herein, for example, a spool.

Figure 2:
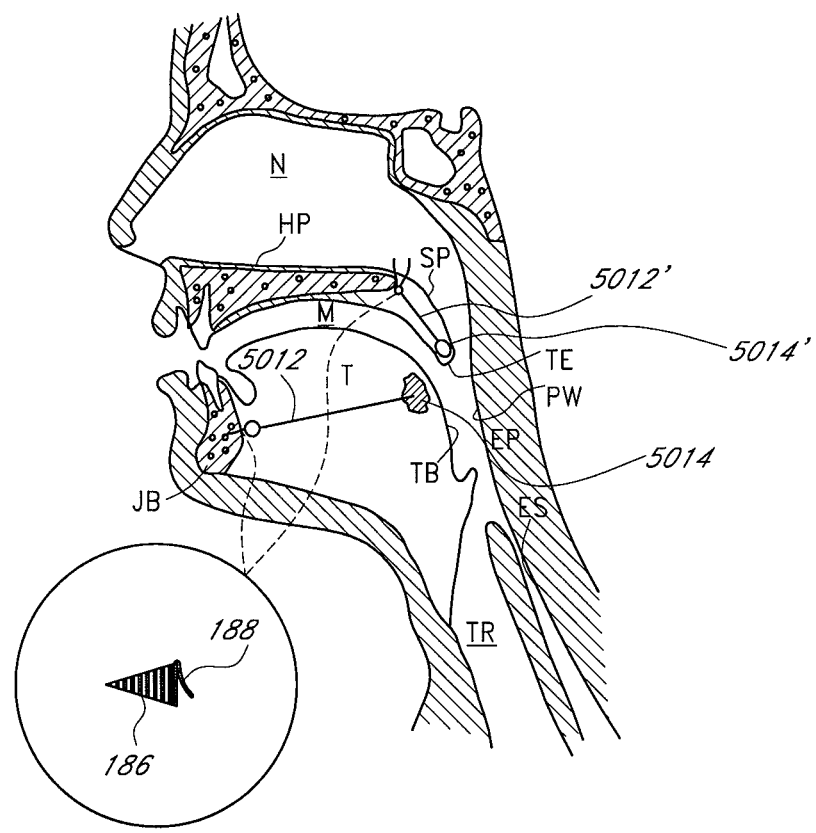
FIG. 2 is a schematic diagram showing one example of a securement assembly that may be used with a tongue or hyoid suspension system, according to one embodiment of the invention.
Figure 5:
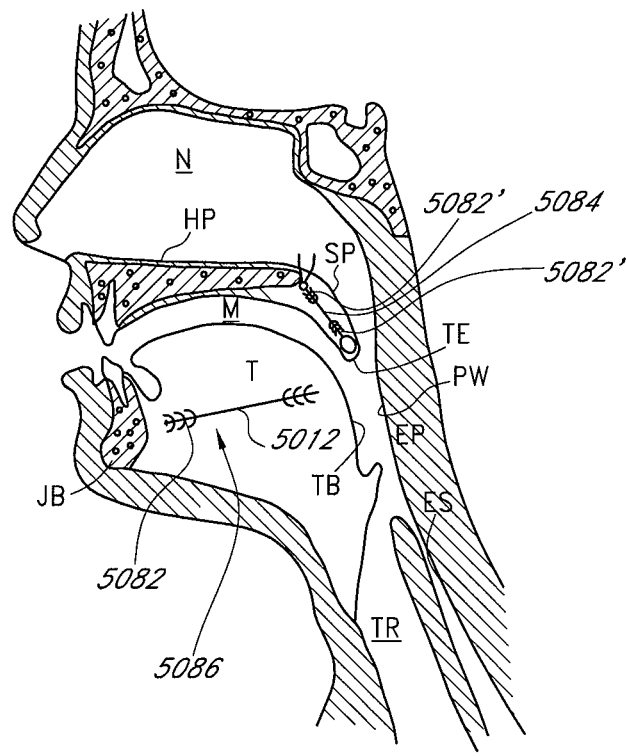
FIG. 5 shows a tongue suspension system with an elongated member comprising a double-ended anchor, according to one embodiment of the invention.

In some embodiments as shown in FIG. 5, soft palate implants, such as those disclosed in Conrad may include one or more anchors 5082' selected from those disclosed in the Frazier '519 publication (e.g., FIGS. 63-69 of the Frazier '519 publication) replacing the one or more tissue ingrowth ends of the expandable member, for example, as illustrated in Conrad FIGS. 1-2.

Figure 6A:
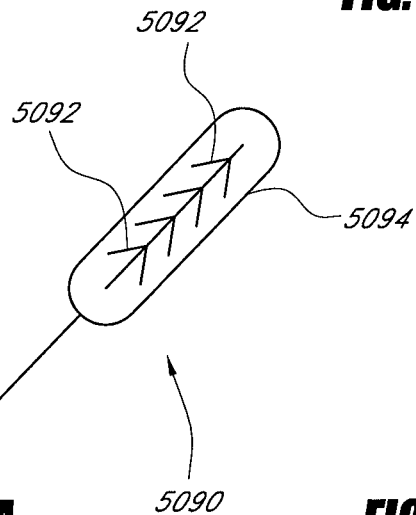
FIGS. 6A-B illustrate an anchor with a plurality of barbs that may be self-expandable, according to one embodiment of the invention.
Figure 6B:
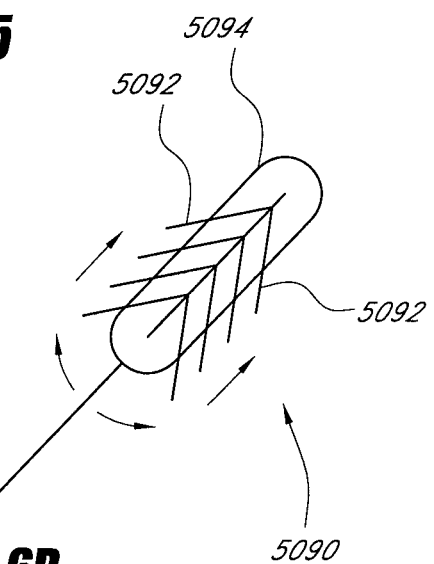

Another embodiment of an improved tongue or palatal suspension system comprises one or more tissue-engaging anchors 5090 as illustrated schematically in FIGS. 6A-B herein. The anchor 5090 may be deployed distally, proximally, or both distally and proximally (relative to the position of the tongue or the palate), and connected by a tether that is preferably elongate and flexible in some embodiments. The anchor 5090 may optionally comprise a plurality of "fish bone" shaped barbs 5092 in series extending radially out from and operably connected at one end to the anchor 5090 as illustrated. The angles of the barbs 5092 when fully deployed may range anywhere from about 0 degrees to about 180 degrees with respect to vector of insertion, preferably about 45 degrees to 135 degrees, and most preferably about 60 degrees to about 150 degrees. The angles of the barbs 5092 may be uniform or non-uniform along the length of the implant 5090. Although the barbs 5092 in FIGS. 6A-B are arranged in pairs within a common plane of orientation, in other embodiments the barbs 5092 may be unpaired and/or circumferentially arranged. The barbs 5092 may be made of Nitinol, other metals, one or more polymers, or other suitable material. In some embodiments, the barbs 5092 may be bioabsorbable to decrease tissue irritation as well as to facilitate tissue ingrowth. In some embodiments, at least 1, 2, 3, 4, 5, 6, 7, 8, 9, 10, or more barbs may be present. The anchor 5090 may be predeployed in a first, collapsed configuration, as schematically illustrated in FIG. 6A within a delivery tube (not shown). Upon removal of the delivery tube, for example, within the genioglossus muscle, the barbs 5092 spring outward to engage the tissue, as shown in FIG. 6B. The anchor 5090 may be attached to an adjustable securement assembly as described above and disclosed in the Frazier '519 publication. The adjustability is especially advantageous when the anchor 5090 is placed untensioned, and tensioned at a later time after a healing and tissue ingrowth period. The anchor 5090 disclosed herein may also be configured for use for soft palate implants as disclosed in Conrad, as well as Conrad '307.

Conrad discloses several implants to stiffen the base of the tongue and resist floppy action or lack of tone in the tissue of the tongue near the base. For example, FIG. 8 of Conrad illustrates contracting implants 40 that may be placed in the tongue T in-line with radiating lines A of certain muscles of the tongue (e.g., genioglossus muscles). As the implants 40 contract over time, they urge the tongue T from collapsing toward the pharyngeal wall PW. FIG. 12-13 of Conrad illustrates implants 120 spaced apart for fibrosis to interconnect between the implants 120. FIGS. 14-17 of Conrad illustrate the use of embedded crimps or staples 150 to stiffen and potentially illustrate the tongue base. In the embodiments shown in FIGS. 14-15, the crimps 150 are slightly curved members which are placed in the tongue with concave surfaces opposing the tongue base. The crimping acts to squeeze tissue of the tongue to stiffen the tongue.

Figure 7A:
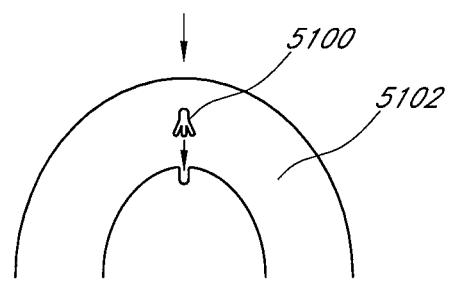
FIGS. 7A-B show an implant comprising a multi-pronged stiffening element, according to one embodiment of the invention.
Figure 7B:
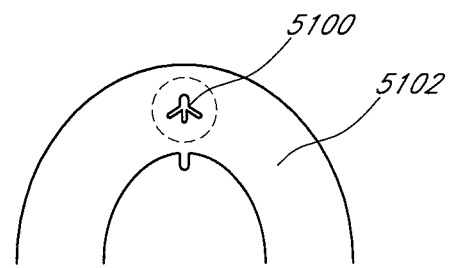

In another embodiment, of the invention, disclosed is a multi-pronged stiffening element 5100, schematically illustrated implanted in a soft palate herein in FIGS. 7A-B. The stiffening element 5100 may have at least about two, three, four, five or more prongs and be implanted, for example, in the tongue, palate, and the like. The stiffening element 5100 increases stiffness within the implanted tissue by stretching the tissue in one or more directions. In some embodiments, the tissue is stretched laterally. In some embodiments, the stiffening element 5100 is trident-shaped as shown. However, one of ordinary skill in the art will appreciate that many other possible shapes are possible. The stiffening element may be expandable after delivery.

Recapturability

Figure 8A:
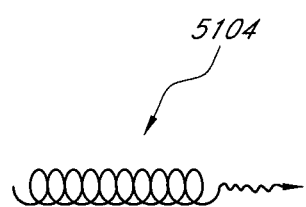
FIGS. 8A-B illustrate a woven tissue implant that can be conveniently removed after implantation, according to one embodiment of the invention.
Figure 8B:
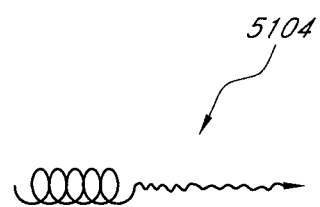

FIGS. 8A-B illustrate an embodiment of an improved woven tissue implant 5104 that can advantageously be easily removed, from, e.g., the tongue or the soft palate. The implant 5104 may be a batten type stiffener or tissue anchor formed from a single strand. The single strand can be woven or knitted into a desired shape, for example, a rod-like structure. The woven tissue implant 5104 may be deployed into tissue to stiffen a particular area and serve a similar function to the implants illustrated in FIGS. 8 and 12-17 of Conrad or implants of the PILLAR® system (Restore Medical), or attached to one or more tethers for use as a tissue anchor or sling. The woven design facilitates tissue ingrowth within the spaces around the woven implant 5014, effectively increasing the surface area of the implant 5104 and increasing the implant's anchoring force. The implant 5104 is most preferably configured to have sufficient structural integrity necessary to anchor tissue. However, the woven implant 5104 is also preferably configured such that pulling on an end of the single strand of the implant with an appropriate force will unwind or unravel the implant 5104 into a long filament (as shown in FIG. 8B) for simple and convenient removal of the implant. The appropriate force required to unwind the implant 5104 is most preferably sufficiently greater than the tensioning force of the tissue on the implant 5104 while deployed in the tongue, palate, or surrounding tissue so that the implant 5104 does not undesirably unwind while deployed. Part or all of the implant 5104 may include a radiopaque marker material.

As illustrated in FIG. 3 of Conrad, the implant may comprise a bioresorbable material 20 positioned between the tissue-engaging end 14a of the elongated member 12a and an anchor 16a. The bioresorbable material 20 may oppose a spring member 12a which may be stretched to create a bias urging ends 14a, 16a of the elongated member 12a toward one another. The bioresorbable material 20 positioned between the tissue-engaging end 14a and a bolt 18a will later resorb into the tissue of the tongue T permitting the end to be urged toward the bolt 18a by the resilience of the spring 12a, tensioning the device.

Figure 9A:
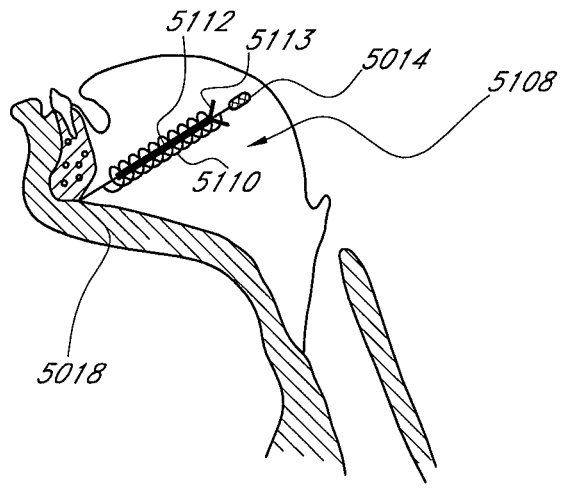
FIGS. 9A-C show a tissue implant that comprises a locking rod, according to one embodiment of the invention.
Figure 9B:
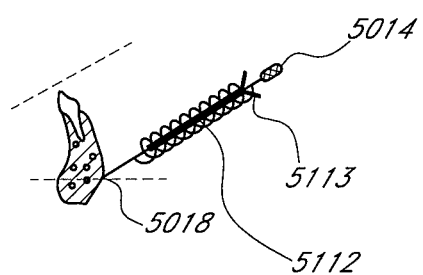
Figure 9C:
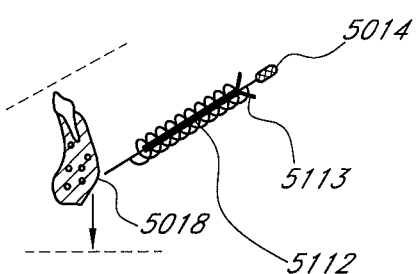

FIG. 9 herein illustrates an improved embodiment of a tether 5108 that may be used with tissue ingrowth implants, such as, for example, those disclosed in Conrad. An improved tether 5108 comprises a locking bar 5112 releasably attached to both the tissue ingrowth end 5014 and the bone anchor 5018 (or both tissue ingrowth ends in some embodiments) and disposed within an elastic member 5110. The elastic member 5110 is preferably connected to an implant or anchor 5014 (such as the tissue ingrowth engaging member of Conrad) at a first end and a securing element 5018 (such as a bone anchor) or another tissue anchor at a second end. The locking bar 5112 may comprise one or more forked or capped ends 5113. The locking bar 5112 may comprise metal, polymer, or other biocompatible material, but preferably has a relatively low elasticity to prevent migration of the implant or anchor 5014 in the acute post-implantation period. During this period, there may be inadequate tissue ingrowth for the implant or anchor 5014 to provide a sufficient anchoring force to tension the tether 5110. Other tethers that can also be used to provide a temporary or permanent anchoring force are disclosed in, for example, the Frazier '519 publication, the '285 provisional application, and the Hirotsuka '752 application.

The locking bar 5112 provides the appropriate anchoring force until adequate tissue ingrowth occurs and the elastic member 5110 can be appropriately tensioned (as an alternative, for example, to the bioresorbable material solution illustrated in FIG. 3 of Conrad). When adequate tissue ingrowth occurs, the locking bar 5112 may be removed via a recapture tool as disclosed elsewhere in the application and the Frazier '519 publication (e.g., at FIGS. 70-72 of the Frazier '519 publication). The locking bar 5112 can be accessed via a surgical procedure and pulled out manually. In other embodiments, the locking bar 5112 may comprise a tether line running to the bone anchor 5018 which can be used with a percutaneous recapture system, such as the system disclosed in the Frazier '519 publication, for removal. A dilator tool can follow the tether to an end of the locking bar 5112, and the locking bar 5112 could then be pulled out. If the locking bar 5112 is made from a smooth material (e.g., a metal or plastic rod) the tether line can be pulled directly to remove the bar without the need for a dilator tool. In some embodiments, the locking bar 5112 may be made of a biodegradable material, such as polylactic acid, polyglycolic acid and the like, that degrades at a rate slow enough to continue to provide anchoring force to the implant 5014 until adequate tissue ingrowth allows the elastic member 5110 to be appropriately tensioned.

Various devices and methods to promote recapturability and removal of a batten implant, such as, for example, implants illustrated in FIGS. 8 and 12-17 of Conrad, implants disclosed in U.S. Pat. No. 6,250,307 to Conrad et al., and the PILLAR® System (Restore Medical) are disclosed. An improved batten-style implant 5120, illustrated in FIGS. 10A-C herein, comprises one or more cap elements 5122. The cap elements 5122 are preferably attached to the proximal end, distal end, or both ends of the batten implant. In some embodiments, the cap element 5122 covers a substantial portion, or even the entire batten implant 5120. The cap element 5122 may be made of, for example, plastic, metal, Dacron, ePTFE, and the like. In some embodiments, the cap element 5122 comprises radiopaque material such that the cap 5122 can be visualized on plain film radiographs. In other embodiments, the cap element 5122 comprises material that can be visualized on ultrasound, magnetic resonance imaging, or other imaging modalities.

The cap elements 5122 can advantageously assist in guiding an implant removal device, such as a cannula 5124, onto the main body of the implant 5120 such that the cutting edges of the removal device 5124 can separate the fibrous encapsulation near the implant surface without cutting into, or otherwise damaging the implant body 5120. The cap elements 5122 may be especially advantageous when the implant 5120 is tethered, for example, when the implant 5120 is used as a tissue anchor to apply traction to the tongue or the palate. Thus, the cap elements 5122 may allow the batten implant 5120 to readily and safely removed from tissue while minimizing tissue trauma and reducing the risk of damage to the implant 5120 complicating removal through increased force or cutting or tearing of the implant 5120.

A method for recapturing a batten implant 5120 will be described. First, trailing sutures 5012 are threaded through a dilator with a cannula assembly 5124, such as a recapture tool depicted in FIGS. 7G to 7J and FIGS. 70-72 of the Frazier '519 publication. Next, the cannula and dilator 5124 (shown schematically as a single cannula for simplicity in FIGS. 10B-C) are advanced over the sutures 5012 and through tissue to the batten implant 5120. In batten implant 5120 embodiments that comprise an imaging marker, the cannula and dilator 5124 may be guided by, for example, an appropriate technique to detect the imaging marker, such as fluoroscopy, ultrasound, CT, MRI, and the like. Fibrous tissue may be dissected from the sutures 5012 using the dilator 5124. Then, in embodiments of implants 5120 that comprise one or more cap elements 5122, the cannula 5124 is advanced over the implant 5120 when the dilator 5124 reaches the cap element 51. The cap element 5122 is preferably configured to be harder in texture than the surrounding peri-implant fibrous tissue, allowing the cannula 5124 to be guided over the implant body 5120 without cutting the softer material of the implant body. Next, the implant 5120 and recapture assembly 5124 is removed.

Delivery Systems

The various embodiments disclosed in Conrad as well as the embodiments of the present invention disclosed herein may be deployed within a delivery system, such as the delivery system disclosed in the Frazier '519 publication (e.g., the delivery system illustrated in FIGS. 62A-D of the Frazier '519 publication). In one embodiment, as illustrated in FIGS. 62B-C of the Frazier '519 publication, a delivery tool comprises a pushrod attached to an actuator handle, the pushrod having a distal position and a proximal position which can be manipulated by a user through the actuator handle. An implant comprising a tissue ingrowth end, static end, and an elongated member, therebetween, such as, for example, an implant illustrated in FIGS. 1-4 of Conrad, may be loaded into the delivery tool by attaching the end(s) of the elongated member to an attachment site on a spool within the delivery tool. When the elongated member is attached to the spool and the dial attached to the spool is rotated, the elongated member, including the tissue ingrowth end, are pulled into the tubular body as the elongated member is wound around the spool. The proximal pulling of the tissue ingrowth end into the delivery tube causes the tissue ingrowth end to retract into a relatively compact delivery profile configuration and into the tubular body. When the actuator handle is moved from the loading position to the deployed position, the actuator handle overcomes the bias of the resistance structure to release the rotation resistance. This allows the spool to freely rotate and to quickly deploy the tissue ingrowth end, followed by the rest of the elongated member, into the tissue. The speed with which the tissue ingrowth end is deployed may affect the degree of tissue engagement by the tissue ingrowth end. In some instances, it is desirable to reduce rotation resistance in the delivery phase compared to the loading phase of the delivery tool usage.

While this invention has been particularly shown and described with references to embodiments thereof, it will be understood by those skilled in the art that various changes in form and details may be made therein without departing from the scope of the invention. For example, in some embodiments, a tongue or soft palate implant may have one or more elements of different embodiments described herein, for example, one or more anchors disclosed in the Frazier '519 publication, '058 provisional application, or Jackson '652 application and one or more adjustment elements described in the Frazier '519 publication, '230 provisional application, or the Dineen '642 application. Furthermore, the invention encompasses other combinations of any or all of the disclosures of the aforementioned references. For all of the embodiments described above, the steps of the methods need not be performed sequentially.

The invention claimed is:

1. A tissue tensioner for treating a condition of a patient's airway comprising:
   a flexible elongate tension member having a first portion and a second portion, the first portion being securable relative to a body tissue; and
   the second portion being connected to a woven or knitted implant formed from a single strand, the implant being configured to be implanted in a patient's tongue, wherein the implant is adapted to unwind or unravel upon pulling of the single strand to facilitate removal from the patient.

2. The tensioner of claim 1, further comprising a cap element covering at least a portion of the woven implant.

3. A method for treating airway obstruction comprising deploying a tissue tensioner as recited in claim 1 into a patient's tongue.

4. A method for treating airway obstruction comprising:
   deploying a tissue tensioner into a patient's tongue, the tissue tensioner comprising a flexible elongate tension member having a first portion secured relative to a body tissue and a second portion comprising a woven or knitted implant comprising a single strand implanted in the patient's tongue; and
   removing the tissue tensioner from the patient by pulling on the single strand with sufficient force such that the implant unravels.

5. The method of claim 4, wherein the first portion is secured relative to the patient's mandible.

6. The method of claim 4, wherein the first portion is secured within the patient's tongue.

* * * * *